US008796213B2

(12) United States Patent
Underwood

(10) Patent No.: US 8,796,213 B2
(45) Date of Patent: Aug. 5, 2014

(54) APOAEQUORIN-CONTAINING COMPOSITIONS AND METHODS OF USING SAME

(75) Inventor: Mark Y. Underwood, Madison, WI (US)

(73) Assignee: Qunicy Bioscience, LLC, Madison, WI (US)

( * ) Notice: Subject to any disclaimer, the term of this patent is extended or adjusted under 35 U.S.C. 154(b) by 432 days.

(21) Appl. No.: 12/672,463

(22) PCT Filed: Mar. 11, 2009

(86) PCT No.: PCT/US2009/036767
§ 371 (c)(1),
(2), (4) Date: Feb. 5, 2010

(87) PCT Pub. No.: WO2009/114597
PCT Pub. Date: Sep. 17, 2009

(65) Prior Publication Data
US 2011/0124562 A1     May 26, 2011

Related U.S. Application Data

(60) Provisional application No. 61/035,443, filed on Mar. 11, 2008.

(51) Int. Cl.
*A61K 38/16*     (2006.01)
*A61P 25/28*     (2006.01)
*A61P 35/00*     (2006.01)
*A61P 9/10*      (2006.01)

(52) U.S. Cl.
USPC ............................ 514/17.7; 424/9.1; 560/350

(58) Field of Classification Search
None
See application file for complete search history.

(56) References Cited

FOREIGN PATENT DOCUMENTS

WO     2006/010004 A2     1/2006

OTHER PUBLICATIONS

Creton et al., Cell Calcium, 22(6): 439-446, 1997.*
Meiser-Stedman, Memory, 15(3):271-279, Apr. 2007.*
Prevagen website, published Apr. 23, 2006 [online]. Copyright 2006 Quincy Bioscience [Retrieved on Aug. 3, 2012] Retrieved from http://web.archive.org/web/20060423160102/http://prevagen.com/.*
Prevagen website, published Oct. 26, 2006 [online]. Copyright 2006 Quincy Bioscience [Retrieved on Aug. 3, 2010] Retrieved from http://web.archive.org/web/20061026090120/http://prevagen.com/.*
Prevagen website, published Sep. 21, 2007 [online]. Copyright 2007 Quincy Bioscience [Retrieved on Feb. 29, 2012] Retrieved from http://web.archive.org/web/20070921105238/http://prevagen.com/.*
Longecity Blog entries dated Sep. 3 and Sep. 5, 2007. Online. Retrieved from: <http://www.longecity.org/forum/topic/17541-prevagen/>. Retrieved on Aug. 15, 2012.*
Amazon.com product reviews dated Oct. 4-20, 2007. Online. Retrieved from: Permalinks <http://www.amazon.com/review/R14TYFS005932N/ref=cm_cr_pr_perm?ie=UTF8&ASI> <http://www.amazon.com/review/R33KJTG88FIQ2/ref=cm_cr_pr_perm?ie=UTF8&ASIN=> <http://www.amazon.com/review/R16C1OBFEU5FND/ref=cm_cr_pr_perm?ie=UTF8&AS>.*
And <http://www.amazon.com/review/R16C1OBFEU5FND/ref=cm_crpr_perm?ie=UTF8&AS> Retrieved on Aug. 15, 2012.*
International Search Report and Written Opinion under date of Jun. 16, 2009 in connection with PCT/US2009/036767.
"Jellyfish Protein Shows Potential to Help with Memory", Reuters. Com [online] Oct. 15, 2008, pp. 1-2; XP002528809; NY, USA; Retrieved from the Internet: URL:http://www.reuters.com/article/pressRelease/idUS219580+15-Oct-2008 +PRN20082025 [retrieved on May 19, 2009].
"Prevagen Fights Aging", Prevagen.Com [online] 2007; XP002528810; Madison, USA; Retrieved from the Internet: URL:http://web.archive.org/web/20080213025013/http://www.prevagen.com/page.aboutus [retrieved on May 19, 2009].
Database WPI Week 200673, tho mas Scientific, London, GB; AN 2006-696533; XP002528811; -& CN 1 752 101 A (Chinese Acad Sci Mar. 29, 2006; abstract; p. 3, lines 1-5, 22-29; p. 5, lines 10-21.
Levere T E et al: "Old age and cognition: Enhancement of recent memory in aged rates by the calcium channel blocker nimodipine"; Neurobiology of Aging, Tarrytown, NY, US; vol. 13, No. 1; Jan. 1, 1992, pp. 63-66; XP024366477; ISSN : 0197-4580 [retrieved on Jan. 1, 1992] abstract, p. 63, left-hand column, paragraph 3; right-hand column, paragraph 1.
Walden Joerg et al: "A calcium antagonist for the treatment of depressive episodes: Single case reports"; Journal of Psychiatric Research, vol. 29, No. 1, 1995, pp. 71-76; XP002530184; ISSN: 0022-3956, abstrct; p. 71, parragraph 1; p. 72, paragraph 1; p. 75, paragraph 4.
Martin M I et al: "Behavioral and analgesic effects induced by adminstration of nifedipine and nimodipine" Pharmacology Biochemistry and Behavior, vol. 55, No. 1, 1996, pp. 93-98; XP002530185; abstrct; p. 93, lef-thand column, paragraph 2; right-hand column, paragraph 1.
Benloucif Susan et al: "Nimodipine potentiates the light-induced suppression of melatonin"; Neuroscience Letters, vol. 272, No. 1, Sep. 3, 1999; pp. 67-71; XP002530186; ISSN: 0304-3940; abstract; pp. 67, right-hand column, paragraph 2; p. 68, left-hand column, paragraph 1.

(Continued)

*Primary Examiner* — Elly-Gerald Stoica
*Assistant Examiner* — Stacey N MacFarlane
(74) *Attorney, Agent, or Firm* — Quarles & Brady LLP

(57) ABSTRACT

Compositions containing apoaequorin and methods for their use in treating symptoms and disorders related to calcium imbalances associated with, for example, sleep quality, energy quality, mood quality, memory quality or pain are provided by the present invention.

9 Claims, 3 Drawing Sheets

(56) References Cited

OTHER PUBLICATIONS

Inouye S et al: "Blue flourescent protein from the calcium-sensitive photoprotein aequorin: Catalytic properties for hte oxidation of coelenterazine as an oxygenase"; FEBS Letters Elsevier, Amsterdam, NL., vol. 580, No. 8; Apr. 3, 2006; pp. 1977-1982; XP025170966; ISSN: 0014-5793 [retrieved on Apr. 3, 2006]; p. 1977, left-hand col. paragraph 1; right-hand column, paragraph 1.

* cited by examiner

APOAEQUORIN-CONTAINING COMPOSITIONS AND METHODS OF USING SAME

CROSS REFERENCE TO RELATED APPLICATIONS

This application represents the national stage application of International Application PCT/US2009/036767 filed Mar. 11, 2009, which claims the benefit of U.S. Provisional Patent Application 61/035,443, filed Mar. 11, 2008, which is incorporated herein by reference in its entirety for all purposes.

STATEMENT REGARDING FEDERALLY SPONSORED RESEARCH OR DEVELOPMENT

Not Applicable.

FIELD OF THE INVENTION

This invention relates generally to compositions useful for the maintenance of calcium homeostasis. In particular, this invention is directed to apoaequorin-containing compositions useful in preventing and/or alleviating diseases or symptoms associated with calcium imbalance.

BACKGROUND OF THE INVENTION

Calcium is the fifth most abundant element in the human body and occurs mainly in the bone. More than 99% of the calcium in the body is stored in the skeleton, which constantly exchanges its supply with the remaining 1% dissolved in body fluids and soft tissue, such as the blood. The control of this exchange is largely dictated by the endocrine system which senses the concentration of ionized calcium in the plasma and directs calcium exchange to maintain this critical balance. Only a small fraction of the 1% of calcium in interstitial fluids and soft tissues is ionized and soluble. The remaining calcium in fluids and tissues is bound to proteins, particularly calcium-binding proteins (CaBPs). CaBPs are known to function in the maintenance of calcium homeostasis.

As the body requires specific concentrations of calcium ions to carry out requisite physiological processes, the maintenance of calcium homeostasis is of critical importance for bodily health. Proper ionic calcium concentrations in plasma and body fluids are understood by the medical community to be critical in bodily functions, including, but not limited to, neuronal excitability, muscle contraction, membrane permeability, cell division, hormone secretion and bone mineralization. A disruption in calcium homeostasis, i.e., a calcium imbalance, is associated with many diseases, syndromes and conditions, including, but not limited to, cancer, heart disease and neurodegenerative disease.

In the past, calcium channel antagonists, which block the flow of calcium between cell interiors and interstitial fluid, have been widely-prescribed as pharmaceutical agents useful in the prevention of calcium-related disorders including hypertension, angina, asthma, migraines and neural deterioration. For example, nimidopine has been found to improve clinical symptomatology and cognitive functions in dementia by alleviating a calcium imbalance which causes neural deterioration. However, many of these calcium channel antagonists have unwanted side effects including, but not limited to, malaise, fluid retention, heartburn, erratic heart rate, dizziness, upset stomach and, in rare cases, fainting, fever and excessive bleeding.

Despite these advances, there is still a need for new and alternative therapeutics which alleviate or prevent calcium imbalance. In particular, pharmaceutical or nutraceutical compositions which have reduced side effects as compared to prior agents are desired and, if discovered, would meet a long felt need in the medical and nutritional health communities.

SUMMARY OF THE INVENTION

The present invention provides compositions which are advantageous in the alleviation and/or prevention of symptoms or disorders associated with calcium imbalance. Such compositions include apoaequorin in combination with acceptable carriers for administration to a subject by a variety of routes.

Accordingly, the present invention is directed to compositions comprising effective amounts of apoaequorin in combination with an acceptable carrier. In certain embodiments, the present invention is directed to nutraceutical compositions including effective amounts of apoaequorin in combination with an acceptable carrier. In certain embodiments, nutraceutical compositions include, in addition to apoaequorin, at least one other component recognized as providing nutraceutical benefit such as, for example, an immune boosting agent, anti-inflammatory agent, anti-oxidant agent, anti-viral agent, or a mixture thereof. Apoaequorin compositions in certain embodiments are provided in a unit dosage form selected from a tablet, a capsule, a solution, a suspension, a syrup, a beverage, an oral or ophthalmic formulation or an injection.

In another aspect, the invention is directed to a method for treating a symptom or disorder associated with calcium imbalance, comprising administering to a subject in need of such treatment an effective amount of apoaequorin.

Methods according to the invention are useful in treating a wide variety of symptoms or disorders associated with calcium imbalance, including but not limited to sleep quality, energy quality, mood quality, pain, memory quality. In certain embodiments, the calcium imbalance is physiologically-related to neuronal excitability, muscle contraction, membrane permeability, cell division, hormone secretion, bone mineralization, or cell death following ischemia. In such methods, apoaequorin is preferably administered to the subject in the form of a nutraceutical composition.

In yet another embodiment, the invention encompasses the use of apoaequorin for the manufacture of a nutraceutical composition for treating a symptom or disorder associated with calcium imbalance in a subject administered the nutraceutical composition. Exemplary symptoms or disorders treated by such compositions include those associated with sleep, energy, mood, pain, or memory.

Accordingly, the present invention further contemplates apoaequorin for use in treating a symptom or disorder associated with calcium imbalance in a subject, including those symptoms or disorders associated with, e.g., sleep, energy, mood, pain, or memory in a subject.

The present invention provides various advantages over prior compositions and methods in that it provides for the general improvement of a subject's mental and physical health.

Other objects, features and advantages of the present invention will become apparent after review of the specification and claims.

DETAILED DESCRIPTION OF THE INVENTION

I. In General

Figure 1:
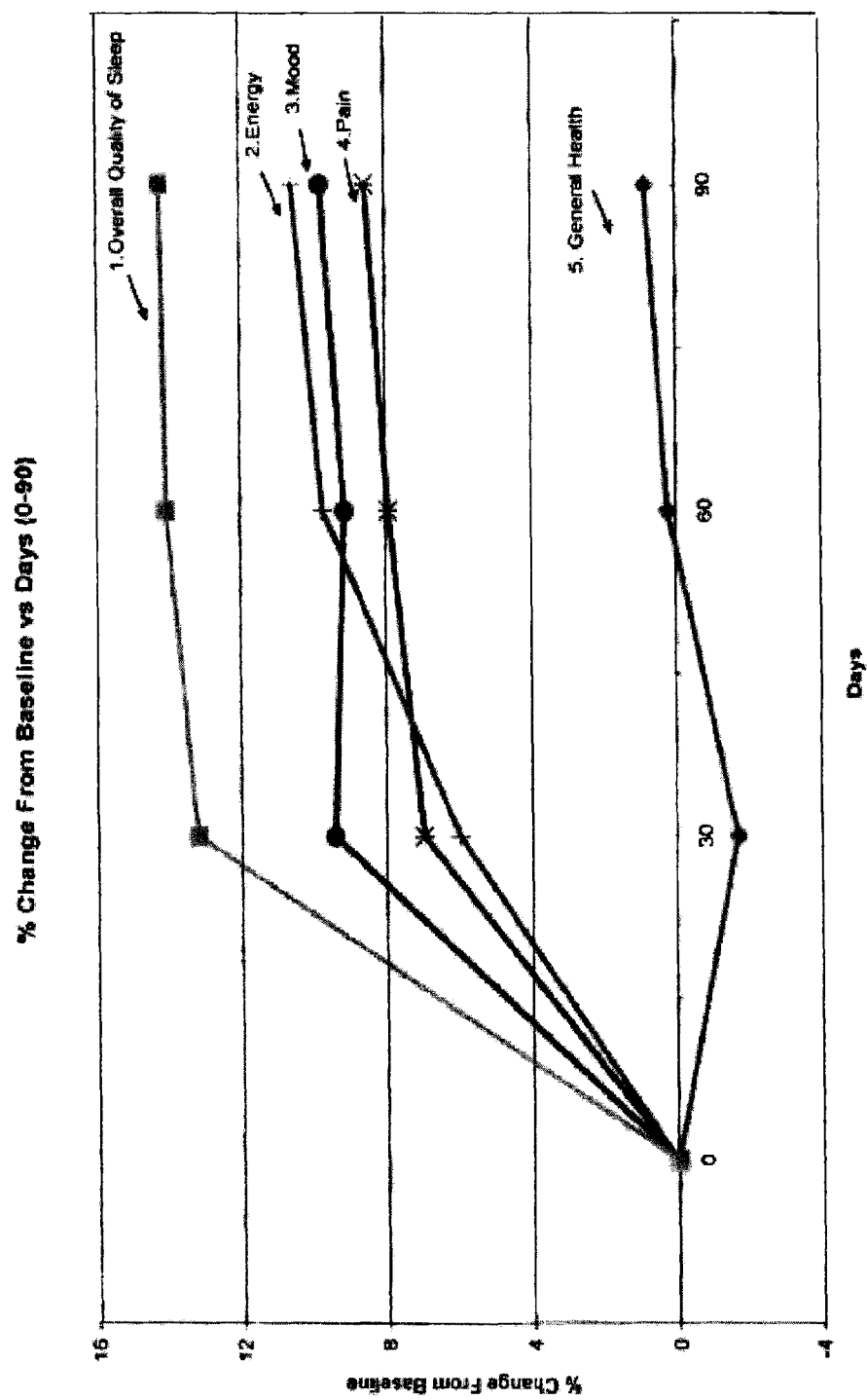
FIG. 1 provides a graph showing the percent change from baseline of scores from areas: overall quality of sleep, energy, mood, pain and general heath vs. days 0 through 90.

Before the present materials and methods are described, it is understood that this invention is not limited to the particular methodology, and materials described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Aequorin is a photo-protein originally isolated from luminescent jellyfish and other marine organisms. The aequorin complex comprises a 22,285-dalton apoaequorin protein, molecular oxygen and the luminophore coelenterazine. When three $Ca^{2+}$ ions bind to this complex, coelenterazine is oxidized to coelentermide, with a concomitant release of carbon dioxide and blue light. Aequorin is not exported or secreted by cells, nor is it compartmentalized or sequestered within cells. Accordingly, aequorin measurements have been used to detect $Ca^{2+}$ changes that occur over relatively long periods. In several experimental systems, aequorin's luminescence was detectable many hours to days after cell loading. It is further known that aequorin also does not disrupt cell functions or embryo development.

Because of its $Ca^{2+}$-dependent luminescence, the aequorin complex has been extensively used as an intracellular $Ca^{2+}$ indicator. *Aequorea victoria* aequorin has been specifically used to: (1) analyze the secretion response of single adrenal chromaffin cells to nicotinic cholinergic agonists; (2) clarify the role of $Ca^{2+}$ release in heart muscle damage; (3) demonstrate the massive release of $Ca^{2+}$ during fertilization; (4) study the regulation of the sarcoplasmic reticulum $Ca^{2+}$ pump expression in developing chick myoblasts; and (5) calibrate micropipets with injection volumes of as little as three picoliters.

Apoaequorin has an approximate molecular weight of 22 kDa. Apoaequorin can be used to regenerate aequorin by reducing the disulfide bond in apoaequorin. The calcium-loaded apoaequorin retains the same compact scaffold and overall folding pattern as unreacted photoproteins containing a bound substrate.

Conventional purification of aequorin from the jellyfish *Aequorea victoria* requires laborious extraction procedures and sometimes yields preparations that are substantially heterogeneous or that are toxic to the organisms under study. Two tons of jellyfish typically yield approximately 125 mg of the purified photoprotein. In contrast, recombinant aequorin is preferably produced by purifying apoaequorin from genetically engineered *Escherichia coli*, followed by reconstitution of the aequorin complex in vitro with pure coelenterazine. Apoaequorin useful in the present invention has been described and is commercially-obtainable through purification schemes and/or syntheses known to those of skill in the art. S. Inouye, S. Zenno, Y. Sakaki, and F. Tsuji. *High level expression and purcation of apoaequorin*. (1991) Protein Expression and Purification 2, 122-126.

The present invention is directed to the administration of apoaequorin-containing compositions to a subject in order to correct or maintain the calcium balance in that subject. The maintenance of ionic calcium concentrations in plasma and body fluids is understood to be critical to a wide variety of bodily functions, including, but not limited to neuronal excitability, muscle contraction, membrane permeability, cell division, hormone secretion, bone mineralization, or the prevention of cell death following ischemia. Disruption in calcium homeostasis, i.e., a calcium imbalance, is understood to cause and/or correlate with many diseases, syndromes and conditions. Such diseases, syndromes and conditions include those associated with sleep quality, energy quality, mood quality, memory quality and pain perception. The study of CaBPs has led to their recognition as protective factors acting in the maintenance of proper ionic calcium levels.

In certain embodiments, the methods of the present invention comprise administering apoaequorin as the sole active ingredient for treating calcium imbalance, for delaying the progression of calcium imbalance, for preventing the onset of calcium imbalance, and for preventing and/or treating the recurrence of calcium imbalance. In other embodiments, the invention provides methods which comprise administering apoaequorin in combination with one or more additional agents having known therapeutic or nutraceutical value. Particularly preferred applications of apoaequorin are in treating one or more symptoms and disorders related to quality of sleep, energy, mood, memory and pain perception.

As used herein, the term "treating" includes preventative as well as disorder remittent treatment. As used herein, the terms "reducing", "alleviating", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cell in contact with apoaequorin. As used herein, administration can be accomplished in vitro, i.e., in a test tube, or in vivo, i.e., in cells or tissues of living organisms, for example, humans. In preferred embodiments, the present invention encompasses administering the compositions useful in the present invention to a patient or subject. A "patient" or "subject", used equivalently herein, refers to a mammal, preferably a human, that either: (1) has a calcium imbalance-related disorder remediable or treatable by administration of apoaequorin; or (2) is susceptible to a calcium imbalance-related disorder that is preventable by administering apoaequorin.

As used herein, the terms "effective amount" and "therapeutically effective amount" refer to the quantity of active agents sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (1) the prevention of a calcium imbalance-related disorder; and (2) the reversal or stabilization of a calcium imbalance-related disorder. The optimum effective amounts can be readily determined by one of ordinary skill in the art using routine experimentation.

In certain preferred compositions for oral administration to subjects, apoaequorin is formulated with at least one acceptable carrier at a dosage of approximately 10 mg/dose, a dose preferably in capsule form, with recommended dosage for a subject approximately 10 mg/day (i.e., one capsule per day).

Compositions according to the present invention include liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, or hydrogels, or onto liposomes, microemulsions, micelles, lamellar or multilamellar vesicles, erythrocyte ghosts or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including parenteral, pulmonary, nasal and oral. In certain embodiments, the composition is administered parenterally, paracancerally, transmucosally, intramuscularly, intravenously, intradermally, subcutaneously, intraperitonealy, intraventricularly, intracranially or intratumorally.

Further, as used herein, "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions and emulsions. Examples of non-aqueous solvents are propylene glycol, polyethylene glycol, vegetable oils such as olive oil and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administrable according to the invention include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal, ophthalmic and oral.

Chemical entities modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the chemical entities solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-entity abducts less frequently or in lower doses than with the unmodified entity.

In yet another method according to the invention, the composition can be delivered in a controlled release system. For example, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity to the therapeutic target, i.e., the brain, thus requiring only a fraction of the systemic dose.

The composition can comprise apoaequorin alone, or can further include a pharmaceutically acceptable carrier, and can be in solid or liquid form such as tablets, powders, capsules, pellets, solutions, suspensions, elixirs, syrups, beverages, emulsions, gels, creams, ophthalmic formulations, or suppositories, including rectal and urethral suppositories. Pharmaceutically acceptable carriers also include gums, starches, sugars, cellulosic materials, and mixtures thereof. The composition containing apoaequorin can be administered to a patient by, for example, subcutaneous implantation of a pellet. In a further embodiment, a pellet provides for controlled release of apoaequorin over a period of time. The composition can also be administered by intravenous, intra-arterial, intramuscular injection of a liquid, oral administration of a liquid or solid, or by topical application. Administration can also be accomplished by use of a rectal suppository or a urethral suppository.

The compositions administrable by the invention can be prepared by known dissolving, mixing, granulating, or tablet-forming processes. For oral administration, apoaequorin or its physiologically-tolerated derivates such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Compositions can be effected both as dry and as wet granules. For parenteral administration (subcutaneous, intravenous, intraarterial, or intramuscular injection), the chemical entity or its physiologically tolerated derivatives such as salts, esters, N-oxides, and the like are converted into a solution, suspension, or expulsion, if desired with the substances customary and suitable for this purpose, for example, solubilizers or other auxiliaries.

Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil or mineral oil. In general, water, saline, aqueous dextrose and related sugar solutions, and glycols such as propylene glycols or polyethylene glycol are preferred liquid carriers, particularly for injectable solutions.

The preparation of compositions which contain an active component is well understood in the art. Such compositions may be prepared as aerosols delivered to the nasopharynx or as injectables, either as a liquid solutions or suspensions; however, solid forms suitable for solution in, or suspension in, liquid prior to injection can also be prepared. The composition can also be emulsified. The active therapeutic ingredient is often mixed with excipients which are pharmaceutically acceptable and compatible with the active ingredient. Suitable excipients include, for example, water, saline, dextrose, glycerol, ethanol, or the like or any combination thereof. In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric, or phosphoric acids, or such organic acids as acetic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like apoaequorin or its physiologically-tolerated derivates are prepared and applied as solutions, suspensions, or emulsions in a physiologically acceptable diluent with or without a pharmaceutical carrier.

In another method according to the invention, the active component can be delivered in a vesicle, in particular, a liposome (see Langer, Science 249:1527-1533 (1990); Treat et al., Liposomes in the Therapy of Infectious Disease and Cancer, Lopez-Berestein and Fidler (eds.), Liss, N.Y., pp. 353-365 (1989).

Salts of apoaequorin are preferably pharmaceutically acceptable salts. Other salts may, however, be useful in the preparation of the compositions according to the invention or of their pharmaceutically acceptable salts. Suitable pharmaceutically acceptable salts include acid addition salts which may, for example, be formed by mixing a solution of apoaequorin with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In addition, apoaequorin-containing compositions described herein may be provided in the form of nutraceutical compositions where apoaequorin prevents the onset of or reduces or stabilizes various deleterious calcium imbalance-related disorders. The term "nutraceutical" or "nutraceutical composition", for the purpose of this specification, refers to a food item, or a part of a food item, that offers medical health benefits, including prevention and/or treatment of disease. A nutraceutical composition according to the present invention may contain only apoaequorin as an active ingredient, or alternatively, may further comprise, in admixture with dietary supplements including vitamins, co-enzymes, minerals, herbs, amino acids and the like which supplement the diet by increasing the total intake of that substance.

Therefore, the present invention provides methods of providing nutraceutical benefits to a patient comprising the step of administering to the patient a nutraceutical composition containing apoaequorin. Such compositions generally include a "nutraceutically-acceptable carrier" which, as referred to herein, is any carrier suitable for oral delivery including aforementioned pharmaceutically-acceptable carriers suitable for the oral route. In certain embodiments, nutraceutical compositions according to the invention comprise dietary supplements which, defined on a functional basis, include immune boosting agents, anti-inflammatory agents, anti-oxidant agents, anti-viral agents, or mixtures thereof.

Immune boosters and/or anti-viral agents are useful for accelerating wound-healing and improved immune function; and they include extracts from the coneflowers, or herbs of the genus *Echinacea*, extracts from herbs of the genus *Sambuca*, and Goldenseal extracts. Herbs of the genus *Astragalus* are also effective immune boosters in either their natural or processed forms. *Astragalus* stimulates development of stem cells in the marrow and lymph tissue active immune cells. Zinc and its bioactive salts, such as zinc gluconate and zinc acetate, also act as immune boosters in the treatment of the common cold.

Antioxidants include the natural, sulfur-containing amino acid allicin, which acts to increase the level of antioxidant enzymes in the blood. Herbs or herbal extracts, such as garlic, which contain allicin, are also effective antioxidants. The catechins, and the extracts of herbs such as green tea containing catechins, are also effective antioxidants. Extracts of the genus *Astragalus* also show antioxidant activity. The bioflavonoids, such as quercetin, hesperidin, rutin, and mixtures thereof, are also effective as antioxidants. The primary beneficial role of the bioflavonoids may be in protecting vitamin C from oxidation in the body. This makes more vitamin C, or ascorbic acid, available for use by the body.

Bioflavonoids such as quercetin are also effective anti-inflammatory agents, and may be used as such in the inventive compositions. Anti-inflammatory herbal supplements and anti-inflammatory compounds derived from plants or herbs may also be used as anti-inflammatory agents in the inventive composition. These include bromolain, a proteolytic enzyme found in pineapple; teas and extracts of stinging nettle; turmeric, extracts of turmeric, or curcumin, a yellow pigment isolated from turmeric.

Another supplement which may be used in the present invention is ginger, derived from herbs of the genus *Zingiber*. This has been found to possess cardiotonic activity due to compounds such as gingerol and the related compound shogaol as well as providing benefits in the treatment of dizziness, and vestibular disorders. Ginger is also effective in the treatment of nausea and other stomach disorders.

Supplements which assist in rebuilding soft tissue structures, particularly in rebuilding cartilage, are useful in compositions for treating the pain of arthritis and other joint disorders. Glucosamine, glucosamine sulfate, chondroitin may be derived from a variety of sources such as Elk Velvet Antler. Marine lipid complexes, omega 3 fatty acid complexes, and fish oil are also known to be useful in treating pain associated with arthritis.

Supplements useful in treating migraine headaches include feverfew and *Gingko biloba*. The main active ingredient in feverfew is the sesquiterpene lactone parthenolide, which inhibits the secretions of prostaglandins which in turn cause pain through vasospastic activity in the blood vessels. Feverfew also exhibits anti-inflammatory properties. Fish oil, owing to its platelet-stabilizing and antivasospastic actions, may also be useful in treating migraine headaches. The herb *Gingko biloba* also assists in treatment of migraines by stabilizing arteries and improving blood circulation.

Although some of the supplements listed above have been described as to their pharmacological effects, other supplements may also be utilized in the present invention and their effects are well documented in the scientific literature.

The invention will be more fully understood upon consideration of the following non-limiting Examples.

EXAMPLES

Example 1

Administration of apoaequorin over a ninety (90) day time course results in improved quality of life for test subjects.

The present analysis, an open-label study, of 32 patients over a 90 day period shows an increase in overall quality of sleep, energy, mood, pain, general health. Changes in performance were measured via a standardized battery of questions. These included assessments of qualitative cognitive test, a sleep index, a headache index and a Quality of Life questionnaire. The study shows improved performance. No participants discontinued the study due to an adverse event.

The results illustrated in FIG. 1 show the percent change from baseline of scores from the areas mentioned; we have excluded the memory scores for another graph. The analysis here is shown as marked on the graph as 1, 2, 3, 4 and 5 vs. days 0 through 90. The graph shows an increase in overall quality of sleep, energy, mood, pain and general health. The baseline was known from a pre-study phase.

Example 2

Administration of apoaequorin over a thirty (30) day time course results in improved quality of life for test subjects.

Figure 2:
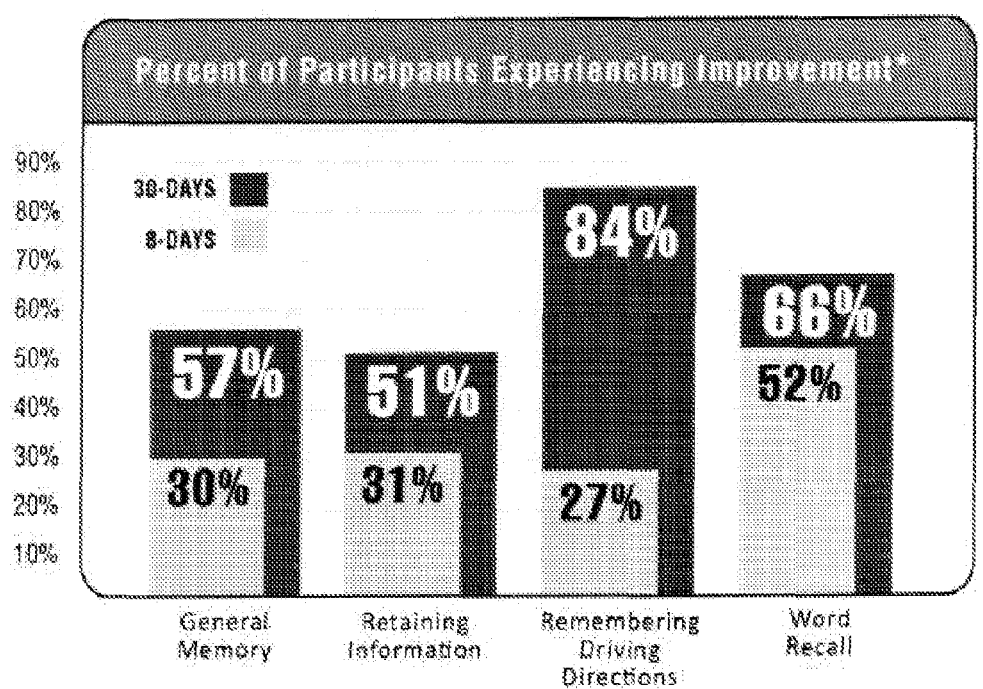
FIG. 2 depicts a graph showing data in which apoaequorin (10 mg) was taken daily by 56 participants. The participants were evaluated from eight days to 30 days. The memory study showed a statistically significant improvement in memory after 30 days (hp<0.05). 57% of participants had improvement in general memory, 51% in retaining information, 84% in remembering driving directions and 66% in word recall. N=56; 66% female, 34% male, mean age=56 years; range 20-78 years.

The present study was an open-label study for 56 participants over a 30 day period. Changes in performance were measured via a memory screening tool. As illustrated in FIG. 2, the study showed improved memory performance as early as eight days but with statistically greater improvement at day 30. No participants discontinued the study due to an adverse event.

Example 3

Administration of apoaequorin over a ninety (90) day time course results in improved cognition for test subjects.

Figure 3:
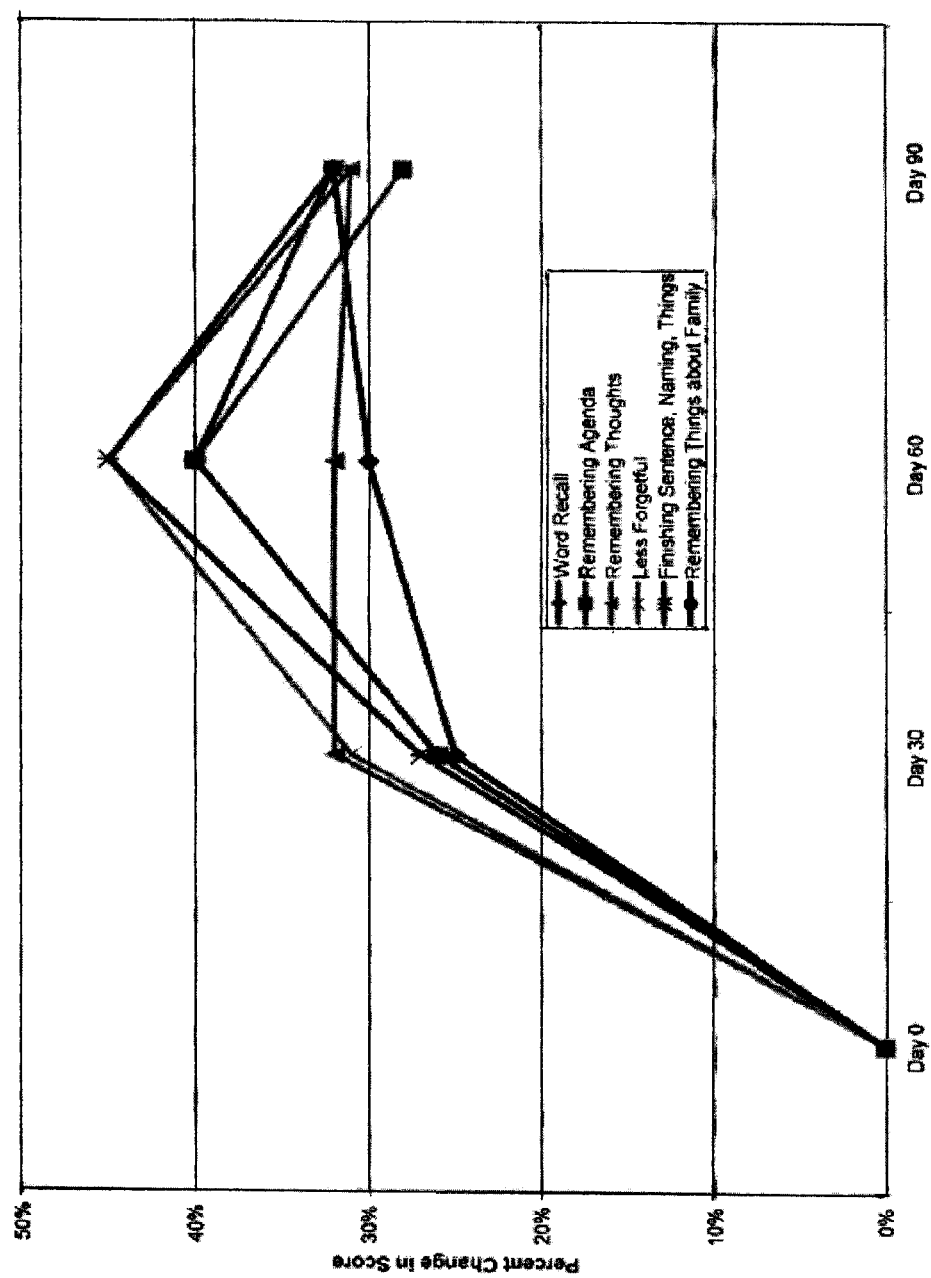
FIG. 3 provides a graph showing the percent change, from baseline, of scores from standardized cognitive battery questionnaire vs. day 0 through 90.

The present analysis, for an open-label study of 32 patients shows an increase in cognitive ability. Changes in performance were measured via a standardized cognitive battery. The study showed improved cognition as early as eight days but with statistically greater improvement at day 30, as well as 60-90. No participants discontinued the study due to an adverse event. The results shown in FIG. 3 demonstrate the significant percent increase from baseline of scores in cognitive ability. Note: Greater than 51% of participants had an increase in cognitive ability.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating a symptom or disorder associated with calcium imbalance, comprising administering to a subject in need of such treatment an effective amount of apoaequorin, wherein said apoaequorin is not administered with its cofactor, coelenterazine.

2. The method according to claim 1, wherein the symptom or disorder associated with calcium imbalance is sleep-related and administration of apoaequorin to said subject improves sleep quality in the subject.

3. The method according to claim 1, wherein the symptom or disorder associated with calcium imbalance is energy-related and administration of apoaequorin to said subject improves energy quality in the subject.

4. The method according to claim 1, wherein the symptom or disorder associated with calcium imbalance is mood-related and administration of apoaequorin to said subject improves mood quality in the subject.

5. The method according to claim 1, wherein the symptom or disorder associated with calcium imbalance is pain-related and administration of apoaequorin to said subject alleviates pain in the subject.

6. The method according to claim 1, wherein the symptom or disorder associated with calcium imbalance is memory-related and administration of apoaequorin to said subject improves memory, as indicated by improved scores on a standardized cognitive assessment.

7. The method according to claim 1, wherein the symptom or disorder associated with calcium imbalance is related to neuronal excitability, muscle contraction, membrane permeability, cell division, hormone secretion, bone mineralization, or cell death following ischemia.

8. The method according to claim 1, wherein apoaequorin is administered to said subject in the form of a nutraceutical composition.

9. The method according to claim 1, wherein apoaequorin is administered to said subject in the form of a capsule for oral delivery.

\* \* \* \* \*